(12) United States Patent
Prien et al.

(10) Patent No.: US 10,390,865 B2
(45) Date of Patent: Aug. 27, 2019

(54) ORTHOPEDIC LOCKING SCREW FOR AN ORTHOPEDIC FASTENING SYSTEM AND METHOD OF SECURING AN ORTHOPEDIC LOCKING SCREW

(71) Applicant: Stryker European Holdings I, LLC, Kalamazoo, MI (US)

(72) Inventors: Ole Prien, Kiel (DE); Thomas Amirov, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/311,610

(22) PCT Filed: May 16, 2014

(86) PCT No.: PCT/EP2014/060089
§ 371 (c)(1),
(2) Date: Nov. 16, 2016

(87) PCT Pub. No.: WO2015/172842
PCT Pub. Date: Nov. 19, 2015

(65) Prior Publication Data
US 2017/0105774 A1   Apr. 20, 2017

(51) Int. Cl.
*A61B 17/86* (2006.01)
*A61B 17/72* (2006.01)
*A61B 17/80* (2006.01)

(52) U.S. Cl.
CPC ........ *A61B 17/725* (2013.01); *A61B 17/8057* (2013.01); *A61B 17/861* (2013.01);
(Continued)

(58) Field of Classification Search
CPC . A61B 17/725; A61B 17/8057; A61B 17/863; A61B 17/8635
See application file for complete search history.

(56) References Cited

U.S. PATENT DOCUMENTS

| 3,731,724 A | 5/1973 | Dorflinger |
| 5,454,813 A | 10/1995 | Lawes |

(Continued)

FOREIGN PATENT DOCUMENTS

| DE | 20307265 U1 | 7/2003 |
| EP | 2228015 A2 | 9/2010 |

(Continued)

OTHER PUBLICATIONS

International Search Report for Application No. PCT/EP2014/060089 dated Aug. 18, 2014.
(Continued)

*Primary Examiner* — Julianna N Harvey
*Assistant Examiner* — Christina Negrelli-Rodriguez
(74) *Attorney, Agent, or Firm* — Lerner, David, Littenberg, Krumholz & Mentlik, LLP

(57) ABSTRACT

An orthopedic locking screw is be configured to be retained inside the bore of an orthopedic implant provided as part of an orthopedic fastening system. The orthopedic locking screw includes a shaft extending axially, a drive member, and a casing secured around an outer surface of the shaft. The casing is formed of a plastically deformable material. The casing has an outer cross-sectional width that is larger than a cross-sectional width of the shaft adjacent the casing. When operably disposed in the bore, an axial and/or radial press-fit pressure is formed between the casing and the bore. A method of securing an orthopedic screw in a bore of an orthopedic implant is provided, in which the shaft is rotated to operably engage the casing to the bore to achieving a deformable press-fit of the casing against the bore.

23 Claims, 5 Drawing Sheets

(52) U.S. Cl.
CPC .......... *A61B 17/863* (2013.01); *A61B 17/866* (2013.01); *A61B 17/8635* (2013.01); *A61B 17/8685* (2013.01)

(56) References Cited

U.S. PATENT DOCUMENTS

| | | | |
|---|---|---|---|
| 6,030,162 A | | 2/2000 | Huebner |
| 6,129,730 A | * | 10/2000 | Bono ................ A61B 17/8047 606/271 |
| 6,355,043 B1 | | 3/2002 | Adam |
| 7,935,138 B1 | * | 5/2011 | Richelsoph ........ A61B 17/8625 606/309 |
| 8,162,998 B2 | | 4/2012 | Schlienger et al. |
| 8,241,287 B2 | | 8/2012 | Prager et al. |
| 2001/0049528 A1 | * | 12/2001 | Kubota ................ A61B 17/742 606/65 |
| 2006/0064095 A1 | | 3/2006 | Senn et al. |
| 2006/0095040 A1 | * | 5/2006 | Schlienger ........... A61B 17/686 606/64 |
| 2006/0149247 A1 | | 7/2006 | Frigg et al. |
| 2008/0255558 A1 | * | 10/2008 | Schlienger ............. A61B 17/72 606/62 |
| 2009/0171396 A1 | | 7/2009 | Baynham et al. |
| 2010/0179550 A1 | | 7/2010 | Schreiber et al. |

FOREIGN PATENT DOCUMENTS

| | | |
|---|---|---|
| WO | 2012107056 A1 | 8/2012 |
| WO | 2013075730 A1 | 5/2013 |

OTHER PUBLICATIONS

International Search Report for Application No. PCT/US2815/861333 dated Jun. 27, 2016.

* cited by examiner

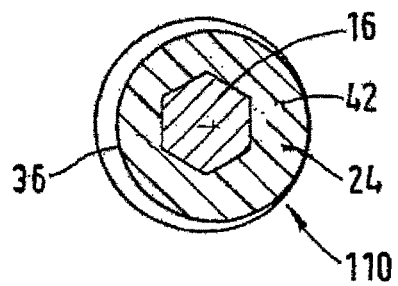
FIG.2A
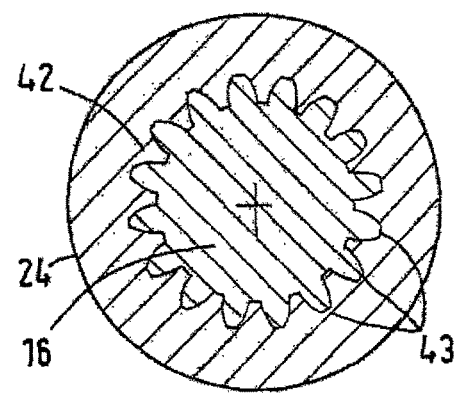
FIG.2B
FIG.2
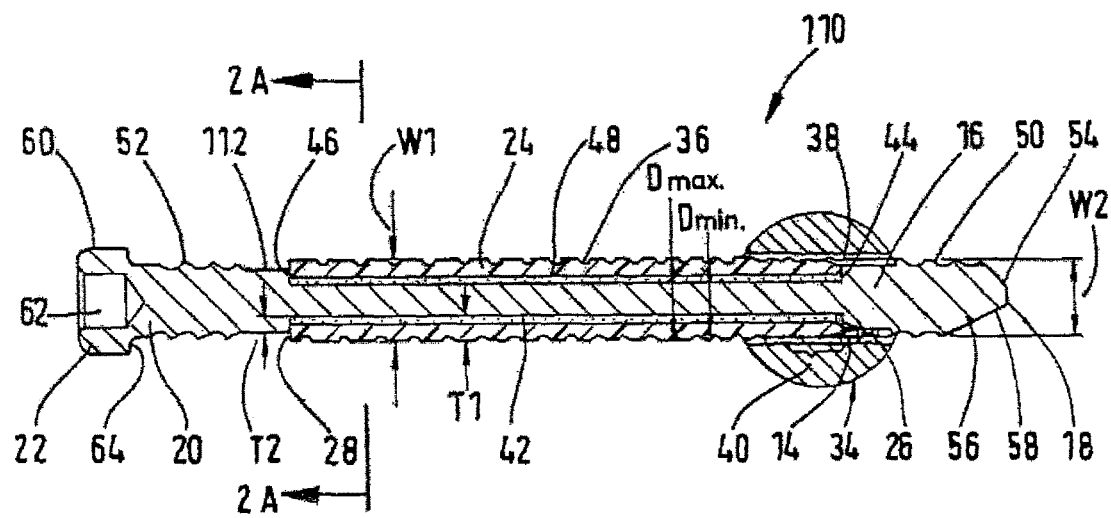

ORTHOPEDIC LOCKING SCREW FOR AN ORTHOPEDIC FASTENING SYSTEM AND METHOD OF SECURING AN ORTHOPEDIC LOCKING SCREW

CROSS-REFERENCE TO RELATED APPLICATIONS

The present application is a national phase entry under 35 U.S.C. § 371 of International Application No. PCT/EP2014/060089 filed May 16, 2014, published in English, the disclosure of which is hereby incorporated herein by reference.

FIELD OF THE DISCLOSURE

The present disclosure relates to an orthopedic locking screw, an orthopedic fastening system including such an orthopedic locking screw, and a method of securing an orthopedic locking screw in a bore of an orthopedic implant.

BACKGROUND OF THE INVENTION

In orthopedic procedures, it is often necessary to secure an orthopedic implant to bone and/or to another orthopedic implant. In such cases, an orthopedic fastening system may be provided in which an orthopedic locking screw is used to secure an orthopedic implant to a bone and/or an orthopedic implant to another orthopedic implant.

One exemplary arrangement that utilizes such an orthopedic fastening system is in the case of an intramedullary bone nail. The intramedullary bone nail is used to secure two or more bone pieces together, and orthopedic locking screws are used to secure the bone pieces to the intramedullary bone nail. One exemplary arrangement of an intramedullary bone nail secured to the bone pieces with locking screws is shown in WO 2013/075730 A1.

Another bone screw disclosed in U.S. Pat. No. 8,162,998 includes a radially expandable sleeve with internal threads that is threaded onto a threaded end of the screw.

However, often there is a small radial gap or interval between the outer diameter of the locking screw and the inner diameter of the bore of the orthopedic implant that operably receives the locking screw. For example, the locking screw may have an average outside diameter of 5.0–0.05 mm and the bore may have an average internal diameter of 5.1+0.2 mm. This gap or interval can give rise to up to 0.1+0.25 mm radial play between the locking screw and the orthopedic implant. This radial play can allow shifting and movement of the bone and/or locking screw relative to the orthopedic implant and/or relative to other bone portions secured by the orthopedic implant. Such shifting and movement may slow down or otherwise have a negative effect on healing of the fracture.

In order to eliminate or minimize this play between the connected parts, it is common to use additional screws. This, however, increases the number of parts used and inserted into the body and may increase the necessary healing time.

SUMMARY OF THE INVENTION

There is a need for an orthopedic locking screw configured to be used as part of an orthopedic fastening system that, in some cases, may reduce or eliminate the amount of shifting and movement between parts of the orthopedic fastening system and/or reduce the number of additional screws needed to sufficiently minimize any such movement.

According to some aspects of the present disclosure, an orthopedic locking screw configured to be secured through a bore includes a shaft extending axially between a first end and a second end. A drive member is disposed at the second end. A casing is secured and rotationally fixed around an outer surface of the shaft. The casing is formed of a plastically deformable material. The casing has a first end proximate the first end of the shaft and a second end proximate the second end of the shaft. The casing has an outer cross-sectional width that is larger than a cross-sectional width of the first end of the shaft adjacent the first end of the casing.

According to some aspects, an orthopedic fastening system includes an orthopedic implant comprising a bore and an orthopedic locking screw configured to be retained inside the bore. The orthopedic locking screw includes a shaft extending axially between a first end and a second end, the first end sized to be received in the bore, a drive member disposed at the second end, and a casing secured and rotationally fixed around an outer surface of the shaft. The casing is formed of a plastically deformable material, and has a first end proximate the first end of the shaft and a second end proximate the second end of the shaft. The casing has an outer cross-sectional width that is larger than a smallest inside cross-sectional width of the bore and forms a press-fit pressure against the bore when operably disposed in the bore. In other arrangements, the orthopedic locking screw may include any one of the embodiments and variations shown and/or described herein, and the orthopedic implant may be any type of orthopedic implant with a bore.

According to some aspects, a method of securing an orthopedic screw in a bore of an orthopedic implant is provided. The method includes the step of providing an orthopedic locking screw including a shaft extending axially between a first end and a second end, the first end sized to be received in the bore; a drive member disposed at the second end; and a casing secured and rotationally fixed around an outer surface of the shaft, wherein the casing is formed of a plastically deformable material, the casing having a first end proximate the first end of the shaft and a second end proximate the second end of the shaft, and wherein the casing has an outer cross-sectional width that is larger than a smallest inside cross-sectional width of the bore. The method further includes the steps of inserting the first end of the shaft into the bore, engaging the casing with the bore, and rotating the drive member to rotate the shaft and the casing so as to operably engage the casing with the bore, thereby achieving a deformable press-fit of the casing against the bore.

In other forms of the method, the orthopedic screw may include any one of the embodiments and variations shown and/or described herein, and the orthopedic implant may include any orthopedic implant with a bore, such as described and/or shown herein.

Any one of these aspects may optionally include any one or more of the following arrangements and/or features in any operably compatible combination and form.

In some arrangements, for example, the orthopedic locking screw may be realized in the form of a threaded or unthreaded bolt.

In some arrangements, the orthopedic implant is, for example, an intramedullary bone nail, with one or more bores extending partially or completely therethrough for receiving a locking screw therein. The orthopedic implant is not limited to an intramedullary bone nail. The orthopedic implant may be, for example, a plate or bone connector, or another type of orthopedic implant.

In some arrangements, the bore optionally defines an internal surface feature, such as an internal thread feature, including one or more internally projecting ribs, tabs, or threads that are configured to engage with the casing (e.g., with external engagement features thereof) to retain and/or advance the screw into and/or through the bore. The internal surface features may define a helical path or may not define a helical path. The bore may be an internally threaded bore. The bore may be a through bore or a blind bore.

In some arrangements, the casing is formed of a material that is able to deform plastically so as to be able to develop a press-fit pressure against an opposing surface feature of the bore, such as an inside surface, edge, and/or an inside thread feature. Generally, the casing may be formed from a material that is more plastically deformable than the screw shaft. The casing may be formed of a rubbery (e.g., polymeric) material, such as rubber or silicon or other polymer. The material of the casing may have a lesser hardness than the opposing inner surface and/or surface features of the bore. The casing may be formed, for example, of a polymer or a metal capable of plastic deformation upon engaging the bore. The press-fit pressure may be semi-resilient such that the press-fit pressure is operable to lockingly grip or otherwise retain the screw in the bore. In some instances, this may provide an angularly stable connection between the orthopedic locking screw and the bore.

In some arrangements, one or more of the each of the shaft, the casing, and the orthopedic implant is formed of a bio-compatible material suitable and/or approved for use as an implant in a human and/or animal. The material of the casing may be softer than the material of at least one of the shaft and the internal surface feature and/or surface of the bore. The material of the casing may include at least one of a polymer and a metal. The material of one or both of the shaft and the orthopedic implant may include at least one of a polymer, a metal, and a ceramic.

In some arrangements, the external surface of the casing is substantially smooth and/or includes substantially smooth areas, which do not include any engagement features. In some arrangements, one or more engagement features are disposed on the outer surface of the casing. An individual engagement feature is configured to operably engage with the bore, for example, to operably engage one or more internal surface features in the bore, such as one or more internal threads, tabs, ridges, and/or edges on the bore, in such a manner so as to retain and/or advance the shaft in the bore with a mechanical interfit. The engagement feature may include a protrusion or a recess that interacts with a thread feature of the bore, for example, in a manner similar to threaded engagement, although the engagement feature need not necessarily be a helical thread. For example, the engagement feature may include projections, such as tabs or ridges. The engagement feature may include recesses, such as grooves. The engagement features may define a helical path or may not define a helical path. The engagement features may be configured to engage the surface features of the bore to retain and/or to advance the shaft in the bore with a mechanical interfit between complementary engagement features on the casing and the bore, such as a mechanical interfit between threads or thread-like features. The engagement feature may be deformable or rigid. The engagement feature may be formed of the same material as the casing, such as by molding or machining the outer surface of the casing. The engagement feature may be formed of a different material than the casing and secured to the outer surface of the casing, such as by molding into the casing material, welding, for example with heat and/or chemicals, and/or adhering, for example with adhesive.

In some arrangements, the engagement feature may include an external thread. The external thread may be a continuous thread or an intermittent thread. The external thread may be a deformable thread. The deformable thread may be molded or machined into the outer surface of the casing. The deformable thread may be formed of the same material as the rest of the casing.

In some arrangements, a minor diameter of the deformable thread is larger than the largest outside diameter of the first end of the shaft and/or any threads formed on the first end of the shaft. The minor diameter of the deformable thread may be larger than a corresponding smallest opening width of the bore, such as the minor diameter of any internal thread features of the bore. In some arrangements, a major diameter of the deformable thread is larger than a major diameter of an internal thread of the bore. In these arrangements, when the casing is operably engaged with the bore, such as by threaded engagement, a radial press-fit pressure is formed between the bore and an outer radial surface of the casing, thereby helping to form a press-fit locking action between the casing and the bore.

In some arrangements, the deformable thread has a variable pitch that varies along the direction of the axis. The pitch may vary from a smaller pitch proximate the first end of the shaft to a larger pitch proximate the second end of the shaft. The pitch may vary continuously or the pitch may vary discontinuously. In these arrangements, when the casing is operably threadedly engaged with the bore, an axial press-fit pressure is formed between the bore and the axial sides of the deformable threads, thereby helping to form a press-fit locking action between the casing and the bore.

In some arrangements, the outer surface of the first end of the casing is tapered radially inwardly toward the outer surface of the shaft. The first end of the casing may be tapered to the same radius or other outer cross-sectional dimension of the adjacent portion of the first end of the shaft so as to have a smooth transition between the outer surface of the first end of the shaft and the outer surface of the first end of the casing. Alternatively, the first end of the casing may have a larger radius or other outer cross-sectional dimension than the adjacent portion of the first end of the shaft so as to form a radially stepped transition between the outer surface of the first end of the shaft and the outer surface of the first end of the casing. The outer surface of the casing may be tubular with a constant cross-sectional dimension, such as being cylindrical, along the entire length thereof or along some less than entire portion thereof.

In some arrangements, the deformable thread has a constant minor diameter along its entire length. The deformable thread may have a variable depth, such as with a minor diameter and/or with a major diameter that increases continuously or discontinuously in the direction from the first end of the casing toward the second end of the casing. The deformable thread may extend continuously or intermittently along the casing. The deformable thread may extend from adjacent the first end of the casing. The deformable thread may have a second end at the second end of the casing or spaced axially from the second end of the casing. Where the first end of the casing is tapered, the deformable thread may have a first end along the tapered portion. The first end of the deformable thread may be spaced from the first end of the casing.

The casing may be secured to the outer surface of the shaft in any manner sufficient to prevent rotational and/or axial sliding of the casing relative to the shaft, for example, when the casing is rotationally engaged against an outer or internal surface of the bore. The casing may be molded directly against the outer surface of the shaft so as to provide a molded securement between the casing and the outer surface of the shaft. The casing may be adhesively secured to the outer surface of the shaft with an adhesive. The casing may be mechanically secured to the outer surface of the shaft, for example, by engagement with projections or other surface features with the shaft, such as threads, ribs, tabs, grooves, and/or scoring. The shaft may have a polygonal or other non-circular profile (i.e., cross-sectional shape transverse to the longitudinal axis of the shaft) that prevents the casing from rotating relative to the shaft.

In some arrangements, the shaft includes at least one groove. The groove may receive some or all of the casing. The inner radial surface of the casing may be secured against the surface of the groove, such as by mechanical interaction, molding, welding, and/or with adhesive.

The groove may extend circumferentially around the shaft (e.g. in the form of a radial groove). Additionally, or as an alternative, the groove may extend axially along the shaft. The groove may have a generally polygonal core profile. The groove may have a generally arcuate core profile, such as circular or oval. Further, the groove may include both arcuate core profiles and polygonal core profiles. The groove may include one or both of a first shoulder proximate the first end of the shaft and a second shoulder proximate the second end of the shaft. The first and/or second shoulders may at least partially secure the casing axially and/or radially on the shaft. The first end of the casing may engage the first shoulder and/or the second end of the casing may engage the second shoulder. The casing may have a thickness larger than a radial depth of the groove such that outer diameter or other outside cross-sectional dimension of the casing is larger than an outer diameter or other outside cross-sectional dimension of the first end of the shaft adjacent the casing.

The casing and/or the shaft may have different cross-sectional shapes (as measured radially and orthogonally to the axis of the shaft). The casing and/or the shaft may be substantially cylindrical, with a substantially circular cross-section (as measured orthogonally to the axis of the shaft). However, the cross-section does not necessarily have to be circular, and may be partially or totally elliptical or have other arcuate shapes. The shaft may have an elongate polygonal profile, such as a rectangular, square, hexagonal, or other polygonal shape or have longitudinal ribs or grooves or other protrusions or recesses.

In some arrangements, the outer cross-sectional width of the casing corresponds to an outside diameter of the casing. If the casing includes a thread feature, such as an external thread feature, the outer cross-sectional width of the casing may be an inner diameter of the thread feature or an outer diameter of the thread feature.

In some arrangements, the cross-sectional width of the shaft is an outside diameter of the shaft. The cross-sectional width of the shaft may be immediately adjacent the first end of the casing. If a thread feature is disposed at the first end of the shaft, the cross-sectional width of the shaft may be an inner diameter of the thread feature or an outer diameter of the thread feature.

In some arrangements, a minor diameter of the external thread on the casing is larger than the largest outside diameter of the first end of the shaft. If a thread is disposed on the first end of the shaft, the minor diameter of the deformable thread may be larger than a major diameter or outside cross-sectional measurement of the thread.

In some arrangements, the drive member includes a head configured to engage with a rotational drive member, such as a screw driver or wrench. The head may have a larger, the same, or a smaller cross-sectional width than the second end of the shaft adjacent the head. The head may form a shoulder that extends radially outwardly from an outer surface of the shaft to an outer surface of the head. For example, the head may have an outside diameter that is larger than the outside diameter of the adjacent portion of the second end of the shaft. However, the head may have a circular cross-sectional shape or a non-circular cross-sectional shape, such as partially or totally elliptical and/or polygonal.

In some arrangements, the shaft includes a forward external thread disposed on the shaft between the first end of the shaft and the first end of the casing and/or a rear external thread disposed on the shaft between the second end of the shaft and the second end of the casing. The forward and rear external threads may be spaced apart from each other axially along the shaft. The forward external thread may be spaced axially from the first end of the casing or may extend completely to the first end of the casing. The rear external thread may be spaced axially from the second end of the casing or may extend completely to the second of the casing. Portions of one or both of the forward and rear external threads may extend underneath the respective ends of the casing. Alternatively, the forward and rear external threads may be connected with each other, for example, underneath the casing.

In some arrangements, the forward external thread is sized to operably engage with an internal thread feature of the bore. In other arrangements, the forward external thread is sized so as to not operably engage the bore. For example, the forward external thread may have a major diameter that is smaller than the smallest inside diameter of any internal thread feature of the bore, such as the minor diameter of an internal thread.

In some arrangements, the first end of the shaft includes a tip, optionally having a self-tapping feature. The tip may be tapered. The taper may come to a point or may be blunt, such as by having a rounded or flat nose. The self-tapping feature may include one or more recesses in the outer surface of the shaft, such as grooves, extending axially from the first end of the shaft. The grooves may extend axially through a portion of the forward external threads. The grooves may be helically wound along the tip. The grooves may be formed so as to scoop away material, such as bone.

Other arrangements and combinations within the scope of the appended claims will be apparent upon review of the attached drawings and the following detailed descriptions of the drawings.

BRIEF DESCRIPTION OF THE DRAWINGS

FIG. 2 is longitudinal cross-sectional view of an orthopedic fastening system including an orthopedic locking screw secured through a bore of an orthopedic implant, in accordance with another aspect of the present disclosure;

FIG. 2A is a transverse cross-sectional view of the orthopedic locking screw along the lines 2A-2A of FIG. 2;

FIG. 2B is a transverse cross-sectional view similar to FIG. 2A showing another possible variant;

DETAILED DESCRIPTION

Figure 1:
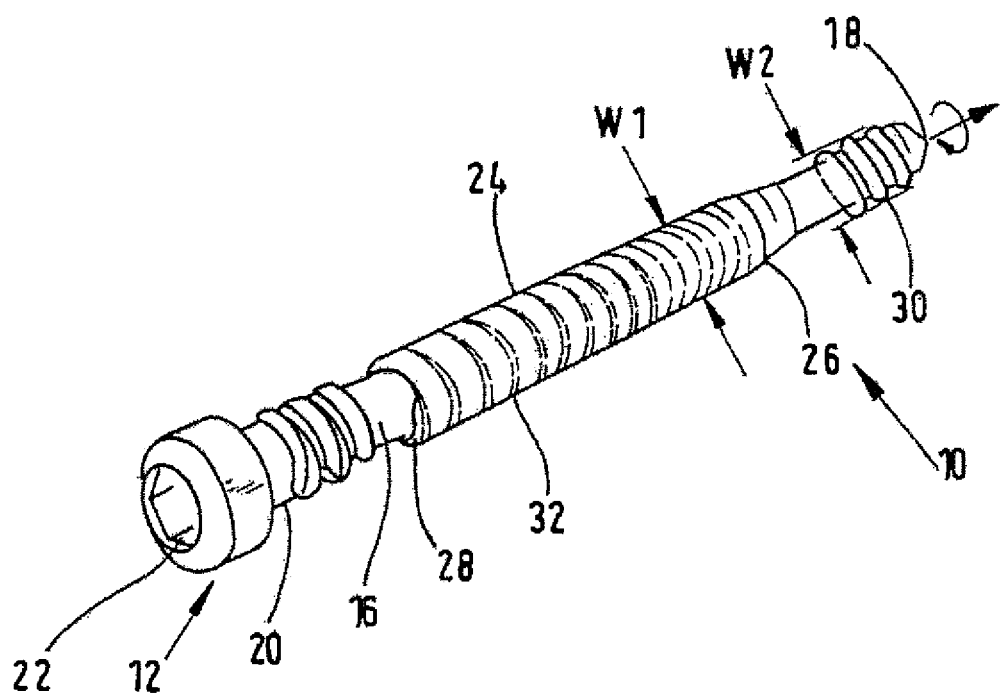
FIG. 1 is a perspective view of an orthopedic locking screw configured to be secured through a bore of an orthopedic implant, in accordance with an aspect of the present disclosure.

Turning now to FIG. 1, an orthopedic fastening system 10 includes an orthopedic locking screw 12 configured to be operably secured through a bore in an orthopedic implant (not shown), such as a bone nail or plate, in order to lock the orthopedic implant into a selected position relative to one or more bones or bone portions. The orthopedic locking screw 12 is configured to provide a press-fit, including a friction fit, with the implant that is configured to prevent or substantially eliminate movement of the orthopedic implant relative to the orthopedic locking screw 12, such as radially in relation to the axis of the screw and/or angularly, in a selected position relative to the orthopedic implant.

The orthopedic locking screw 12 includes a shaft 16 extending axially between a first end 18 and a second end 20. The shaft 16 may have an elongate, tubular form. The profile of the shaft may be polygonal, such as rectangular, square, or hexagonal. The shaft 16 may be generally cylindrical, having a substantially constant diameter extending between the first and second ends; however, in some arrangements, the shaft may have a tubular form with non-circular cross-sections and/or may have varying outside cross-sectional widths. The shaft 16 can have different shapes as long as the orthopedic locking screw 12 is able to operably engage a bore in the implant in such a manner as to be able to retain and, optionally, advance the orthopedic locking screw 12 in and/or through the bore.

A drive member 22 is disposed at the second end 20 of the shaft 16. The drive member 22 may take any form capable of operably engaging with a rotational drive (not pictured), such as a screw driver or wrench, so as to be able to rotate the orthopedic locking screw 12 about the axis of the shaft in order to operably engage the orthopedic locking screw 12 with bone and/or the implant. In FIG. 1, the drive member is in the form of a recess, such as a socket, for receiving a drive member. However, the drive member 22 is not limited to a particular shape or drive arrangement. For example, the drive member 22 may have other shapes, such as having a square or hexagonal circumference for being received in a wrench or a socket, or may have a socket adapted to receive a square or hexagonal drive, or a slot for receiving a screw driver.

A casing 24 is secured around an outer surface of the shaft 16. The casing 24 may be secured to the shaft 16 so as to be rotationally fixed with respect to the shaft 16. The casing 24 is formed of a plastically deformable material, such as plastic or a relatively soft metal. The casing may be formed of a rubbery material, such as rubber or silicon. The casing 24 is secured to the shaft 16 in a manner configured to prevent one or both of axial slipping and radial slipping along the shaft 16 when operatively engaging the implant (i.e., a bore thereof). For example, the casing 24 may be secured by molding to the shaft 16, adhesive, welding, and/or with mechanical fasteners. The casing 24 may be prevented from circumferential slipping by mechanical interaction with a polygonal shaped profile of the shaft 16.

The casing 24 has an outer surface that is sized slightly larger than the smallest inside opening space through the implant so as to form a press fit with the implant. The press fit reduces or eliminates radial shifting and movement of the orthopedic implant relative to the axis of the locking screw 12, thereby minimizing the play between the locking screw, the orthopedic implant, and/or bone portions connected thereby. The press fit optionally also may angularly lock the orthopedic locking screw 12 in a selected position in the implant. The casing 24 optionally has an outer cross-sectional width W1 that is larger than a corresponding largest outer cross-sectional width W2 of the shaft 16 between the first end 18 and the second end 20. The press-fit may include axial and/or radial components.

The casing 24 extends axially along a medial portion of the shaft. In more detail, the casing 24 extends a between a first end 26 and a second end 28. The first end 26 is located proximate the first end 18 of the shaft 16. The second end 28 is disposed proximate the second end 20 of the shaft. The casing 24 has a continuous unbroken outer circumferential surface extending between the first and second ends 26 and 28. The first end 26 of the casing 24 is spaced axially from the first 18 of the shaft 16. The second end 28 of the casing 24 is spaced axially from the second end 20 of the shaft 16. The material forming the casing 24 may be a bio-compatible material suitable for use as an implant in the human body. The outer surface of the casing 24 may be substantially smooth. Additionally or alternatively, one or more external engagement features 32, such as ribs, tabs, or threads may optionally be formed on the outer surface of the casing 24 configured to operably engage, for example, with internal thread features of a bore of the implant. The engagements features 32 may define a helical path or may not form a helical path, and may take any form arranged to operably engage the thread feature of the implant bore so as to advance and/or retain the casing therein. The engagement features 32 may take the form of one or more external threads, such as the deformable thread described elsewhere herein.

A forward external thread 30 or other type of thread engagement feature, such as ribs, tabs, or grooves, may optionally be disposed on the first end 18 of the shaft 16. The forward external thread 30 may be sized to engage a complementary thread feature of an implant bore. Alternatively, the forward external thread 30 may have a major diameter that is smaller than the smallest inside cross-sectional opening through the implant bore, such as a minor diameter of internal threads in the bore. The forward external thread 30 may be operably engaged with a bore through bone disposed behind the bore. In this manner, the forward external thread 30 may be used, for example, to draw the shaft 16 and the casing 24 through the implant bore. As the casing 24 advances through the implant bore, the outer surface of the casing 24 deformably engages with the inner surface or surfaces of the implant bore. The deformable engagement creates a press-fit pressure, for example with a friction fit, that the orthopedic bone screw 12 angularly and/or axially in a selected position in the implant.

Turning now to FIG. 2, another arrangement of an orthopedic fastening system 110 includes an orthopedic locking screw 112 and an orthopedic implant 34, such as an intramedullary nail, that defines a bore 14. The orthopedic locking screw 112 is similar to the orthopedic locking screw 12 in that it includes a shaft 16 extending between first and second ends 18 and 20, a drive member 22 disposed at the second end 20, and a casing 24 secured around an outer surface of the shaft 16. The descriptions thereof are not repeated here for brevity, but reference is made to the previous description in view of the following additional or alternative arrangements.

The bore 14 of the orthopedic implant may be smooth and/or include an internal surface feature, such as an internal thread, having a radially internal arrangement suitable for operably engaging external threads or any other engagement structures on the locking screw 12, for example configured to retain and, optionally, advance any of the orthopedic locking screws disclosed herein upon rotating the locking screw inside the bore. Thus, for example, the bore 14 may in some embodiments be formed of a thin bore that does not have helical threads but has edges that interact with external helical threads or thread-like features to advance and/or retain an orthopedic locking screw. In other embodiments, the bore 14 may include one or more radially internally projecting protrusions that are similarly able to operably interact with external helical threads or thread engagement features. In yet further embodiments, the bore 14 may include one or more helical internal threads, either alone, or in combination with other thread-like features.

The orthopedic locking screw 112 of FIG. 2 is operably engaged within the bore 14 such that the casing 24 forms a press-fit against the bore 14. The press-fit is configured to prevent or substantially eliminate movement of the orthopedic implant 34 relative to the orthopedic locking screw 112, such as radially in relation to the shaft 16 and/or angularly, in a selected position relative to the orthopedic implant 34. Thus, the press fit reduces or eliminates radial shifting and movement of the orthopedic implant 34 relative to the axis of the locking screw 112, thereby minimizing the play between the locking screw, the orthopedic implant, and/or bone portions connected thereby. The press fit optionally also may angularly lock the orthopedic locking screw 112 in a selected position in the bore 14.

The orthopedic implant 34 may be formed of a biocompatible material suitable and/or approved for use as an implant inside a human body. In some arrangements, the orthopedic implant 34 is formed of metal, plastic, and/or ceramic. The orthopedic implant may be any type of orthopedic implant. Some exemplary types of orthopedic implants include bone nails and plates.

In this arrangement, the casing 24 includes a thread engagement feature in the form of one or more deformable threads 36 disposed along the outer surface of the casing 24. The deformable thread 36 is an exterior thread having a major diameter Dmaj and a minor diameter Dmin in a manner well understood in the threading art. The shaft 16 and the casing 24 are shown having generally cylindrical shapes with circular cross-sections (as viewed transverse to the axis of the shaft 16); however, it is understood that the shaft 16 and casing 24 are not limited to cylindrical shapes, but may have other tubular and/or non-cylindrical shapes. The use of the terms major and minor diameter are therefore not to be construed as limiting to purely circular cross-sections, but refer rather to the diameter of the circumscribed circle upon, for example, rotating the shaft 16 about its longitudinal axis. The deformable thread 36 may be a continuous thread or it may be a discontinuous thread defined by a plurality of thread portions with intermittent breaks or interruptions therebetween. For example, if the casing 24 has a polygonal cross-section, such as a generally square cross-section, the deformable thread 36 may be defined by intermittent thread portions defined through the outside corners of the cross-section. Of course, other shapes and arrangements are also possible with the same understanding.

The deformable thread 36 is configured to engage with one or more interior thread features, such as one or more interior threads 38, in the bore 14 in a manner configured to cause at least one or both of a radial press-fit pressure and an axial press-fit pressure. As with the orthopedic locking screw 12, the outside diameter W1 of the casing is larger than the outside diameter W2 of the first end 18 of the shaft 16 so that an outer surface of the casing 24 will deformably engage an internal surface of the bore 14.

In order to optionally achieve a radial press-fit pressure, at least one outside cross-sectional width of the casing 24, such as either the major diameter Dmaj or the minor diameter Dmin, may be sized to be larger than a corresponding smallest inside cross-sectional opening of the bore 14, such as the corresponding minor diameter or the major diameter of the internal thread 38 if the bore is internally threaded. Thus, the major diameter Dmaj of the deformable thread 36 may be larger than the major diameter of the internal thread 38. Additionally or alternatively, the minor diameter Dmin of the deformable thread 36 may be larger than the minor diameter of the internal thread 38.

In order to optionally achieve an axial press-fit pressure, the deformable thread 36 may have a variable pitch along the length of the casing 24. For example, the deformable thread 36 has a smaller pitch at or near the first end 26 of the casing 24 and increases continuously to a larger pitch at or near the second end 28 of the casing 24. However, other pitch variations capable of causing an axial press-fit pressure with the internal threads 38 are also possible and contemplated, such as a discontinuous variation of the pitch, a pitch that decreases from the first end 26 toward the second end 28, or other pitch variations. In this arrangement, the internal threads 38 axially engage and increasingly deform the axial walls of the deformable thread 36 as the thread 36 is advanced through the bore 14, thereby giving rise to a variable, and in this case, increasing, axial press-fit pressure as the orthopedic locking screw 112 is advanced through the bore 14. The minor diameter Dmin of the deformable thread 36 is constant along the length of the thread; however, in other arrangements, the minor diameter Dmin may vary along the length, such as by increasing continuously or discontinuously from the first end 26 toward the second end 28.

In the arrangement of FIG. 2, the deformable thread 36 includes both a continuously increasing pitch (from the first end 26 toward the second end 28) to create an axial press-fit pressure and is sized such that the minor diameter Dmin is larger than the minor diameter of the internal thread 38 to create a radial press-fit pressure. However, other embodiments may include only one or the other feature so as to form only an radial press-fit pressure or an axial press-fit pressure if desired. The deformable thread 36 in this arrangement extends continuously from adjacent the first end 26 of the casing 24 to the second end 28 of the casing 24 as shown in the drawing.

The first end 26 of the casing 24 is optionally tapered radially inwardly, as at 40, toward the outer diameter of the front end 18 of the shaft 16 immediately adjacent the first end 26 of the casing 24. In this arrangement, the deformable thread 36 runs out at a location along the taper 40 before reaching the first end 26, such that the deformable thread 36 has a first end spaced along the taper 40 adjacent to and spaced from the first end 26 of the casing. Alternatively, the thread 36 may run entirely to the first end 26 of the casing 24. In some arrangements, the taper 40 is such that there is a smooth transition between the first end 26 of the casing 24 and the shaft 16. In other arrangements, the first end 26 of the casing 24 may have a larger diameter than the adjacent portion of the shaft 16 so as to form a radially stepped transition. The remaining portion of the outermost diameter of the casing 24 may be substantially cylindrical from the taper 40 to the second end 28 or may have a different taper or other width variations. Alternatively, the outermost diameter of the casing 24 may be substantially cylindrical along the entire axial length between the first end 26 and the second end 28.

A groove 42 extends circumferentially around and axially along the outer surface of the shaft 16. The casing 24 is disposed in the groove 42 such that the groove 42 helps secure the casing 24 on the outer surface of the shaft 16. The groove 42 may have a continuous polygonal core profile, such as a rectangle, square, or hexagon, a continuous arcuate profile, such as circular or oval, or both polygonal and arcuate profiles. In the exemplary arrangement of FIG. 2, the groove 42 has a polygonal core profile, as illustrated in FIG. 2A (the casing 24 has an asymmetric appearance in the cross-sectional view of FIG. 2A due to its outer threading). The polygonal core profile is a hexagonal profile that extends continuously along the entire axial length of the groove 42. In some arrangements, the groove 42 and/or other portions of the shaft may have other core profile shapes, such as star or gear tooth shape formed by elongate ribs 43 or other shaped protrusions or recesses, as shown in FIG. 2B.

The groove 42 has a smaller outside diameter than the adjacent portions of the shaft 16. The groove 42 in this arrangement extends radially completely around the outer circumference of the shaft 16. The groove 42 extends axially from a first radial shoulder 44 proximate the first end 18 of the shaft 16 to a second radial shoulder 46 proximate the second end 20 of the shaft 16. The entire axial length of the casing 24 is received within the groove 42. The first end 26 of the casing abuts the first radial shoulder 44. The second end 28 of the casing abuts the second radial shoulder 46. Thus, the radial shoulders 44 and 46 mechanically retain the casing axially fixed along the length of the shaft 16. The casing 24 has a thickness T1 that is larger than the radial dimension T2 of the groove 42 such that the outer circumferential surfaces of the casing 24 project radially beyond the outer circumferential surfaces of the adjacent first and second ends 18 and 20 of the shaft 16, in accordance with the previous description. A radially inner surface of the casing 24 may additionally or alternatively be secured against the radially outer surface of the groove 42 by other fastening connections 48, such as an adhesive, or an over molded connection, welds, or mechanical fastening features.

A forward external thread 50 is disposed on the shaft 16 between the first end 26 of the casing 24 and the first end 18 of the shaft 16. A rear external thread 52 is disposed on the shaft 16 between the second end 28 of the casing 24 and the second end 20 of the shaft 16. In some arrangements, either or both of the external threads 50 may be omitted, as shown for example with regard to the orthopedic locking screw 12. The forward external thread 50 may have a major diameter that is smaller than the minor diameter Dmin of the deformable thread 36. In some arrangements, the forward external thread 50 is sized so as to not operably engage the bore 14 but is configured mainly for engaging with bone on either or both sides of the bore 14. For example, the major diameter of the forward external thread 50 is smaller than the minor diameter of the internal thread 38 so that the forward external thread does not operably engage the internal thread 38 but can be pushed through the bore 14 without interference. In other arrangements, however, the forward external thread 50 is sized to operably engage the bore 14. For example, major diameter of the forward external thread 50 may be larger than an minimum opening width through the bore 14. The rear external thread 52 may have a major diameter equal to or larger or smaller than the forward external thread 50. The rear external thread 52 may be configured to engage a bore through the bone behind the advancement of the sheath 24. In one arrangement, the major diameter of one or both of the rear external thread 52 and the forward external thread 50 is the same as the major diameter Dmaj of the deformable thread 36 along a cylindrical path. The forward external thread 50 is spaced apart axially from the rear external thread 52. The forward external thread 50 is spaced axially from the first end 26 of the casing 24. The rear external thread 52 is spaced axially from the second end 28 of the casing 24. However, in other arrangements, forward external thread 50 may extend to and/or underneath the first end 26 of the casing 24 and/or the rear external thread 52 may extend to and/or underneath the second end 28 of the casing 24. In yet further arrangements, the forward and rear external threads 50 and 52 may be connected as part of a single thread with a middle portion disposed partially or wholly underneath (i.e., radially inwardly from) the casing 24.

A tip 54 is optionally disposed at the first end 18 of the shaft 16. The tip 54 may be tapered to a point or to a blunt nose, such as a rounded, flat, or truncated nose. The tip optionally includes a self-tapping feature 56 for tapping a bore into bone. The self-tapping feature 56 includes at least one, and optionally a pair of diametrically opposite axial grooves 58 extending along the tip 54 through at least a portion of the forward external thread 50. The axial grooves 58 may be at least partially helically wound. The axial grooves 58 may act to scoop away bone or other material as the orthopedic locking screw 112 is rotated and advanced into the bone.

The drive member 22 optionally includes a head 60 disposed at the second end 20 of the shaft 16. The head 60 is configured to engage with a rotational drive member. For example, the head 60 includes a polygonal socket 62 configured to receive a complementary rotary drive (not shown). Other drive configurations may also be used. The head 60 has a larger diameter than the adjacent second end 20 of the shaft 16, thereby forming a shoulder 64 extending radially outwardly from the outer circumferential surface of the second end 20 of the shaft 16 to the outer circumferential surface of the head 60. In other arrangements, the head 60 may be circumferentially smaller than or the same size as the second end 20 of the shaft 16 and/or may include circumferential engagement surfaces, such as having a hex head outer circumferential shape. The head 60 is not limited to the arrangements expressly described, and other arrangements for operably engaging a rotational drive tool may be used.

Figure 3:
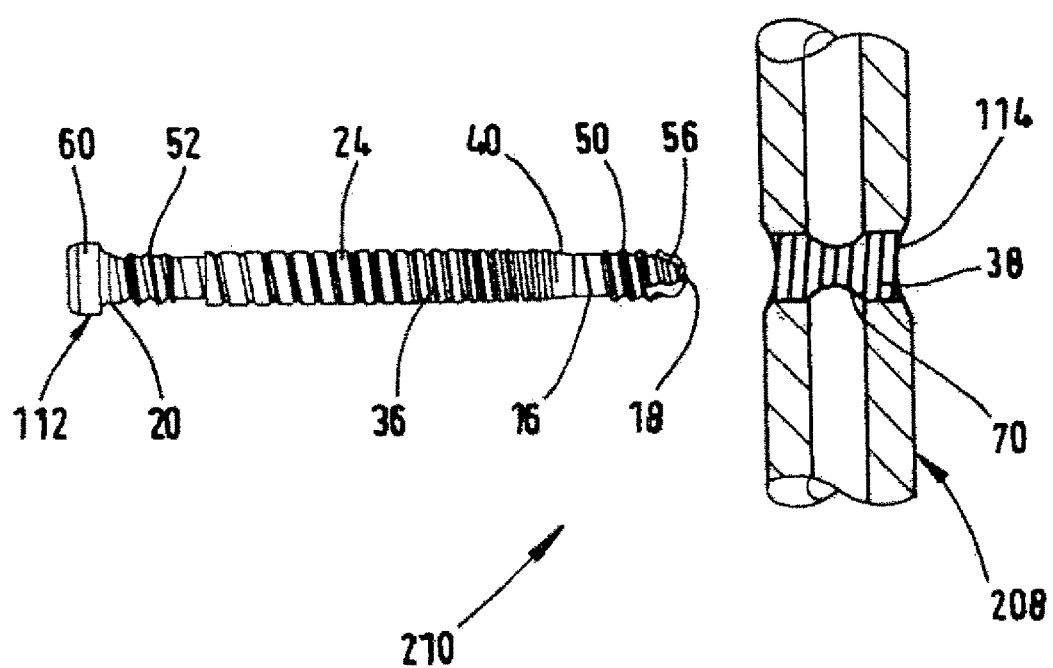
FIG. 3 is a side view shown partly in cross-section of an orthopedic fastening system including the orthopedic locking screw of FIG. 2 (shown in side view) configured to be secured through an orthopedic implant (shown in cross-section), in accordance with another aspect of the present disclosure.

Turning now to FIG. 3, another orthopedic fastening system 210 includes the orthopedic locking screw 112 and an exemplary orthopedic implant 208. However, the orthopedic locking screw 12 could also be used in combination with the orthopedic implants of any of the Figures shown herein as part of this orthopedic fastening system. The orthopedic implant 208 may have any of various specific forms.

The orthopedic implant 208 includes an exemplary bore 114, although the orthopedic implant 208 may include any number of such bores 114. The bore 114 is a through bore extending transversely through the orthopedic implant 208 from a first side to a second side. The bore 114 is internally threaded, including an internal thread 38 helically wound along an inner circumferential surface of the bore. Further, the bore 114 includes a circumferential rib 70 extending around and projecting radially inwardly from the inner circumferential surface of the bore. The circumferential rib 70 is spaced medially through the bore 114, such as being spaced half way between the first and second sides of the bore 114. The internal thread 38 traverses the inner circumferential surface of the circumferential rib 70.

The orthopedic locking screw 112 is sized such that the forward external thread 50 and the deformable thread 36 operably engage the interior thread 38. The forward external thread 50 optionally is configured to receive the inner circumference of the circumferential rib 70 within the groove of the thread. Similarly, the deformable thread 36 optionally is configured to at least partially receive the inner circumference of the circumferential rib 70 within the groove of the thread. However, it is not necessary for the deformable thread 36 to perfectly match the configuration of the internal thread 38 because it can deform to adjust to the internal thread 38.

In one exemplary embodiment, the orthopedic locking screw 112 preferably has an overall length of between 125 mm and 5 mm, and more preferably between approximately 70 mm and 50 mm. The casing 24 preferably has a length of between 100 mm and 3 mm and more preferably between approximately 40 mm and 30 mm. The casing 24 preferably an outside diameter of between 52 mm and 0.9 mm, more preferably between 22 mm and 5 mm, and most preferably between approximately 5.0 mm and 5.2 mm. In one arrangement, the deformable thread 36 preferably has a major diameter of between 51 mm and 0.8 mm, more preferably between 21 mm and 4 mm, and in some arrangements approximately 5.5 mm, a minor diameter of between 50 mm and 0.7 mm, more preferably between 20 mm and 3 mm, and in some arrangements approximately 4.5 mm and a variable pitch that varies continuously along the axial length of the casing from between approximately 0.5 to 2 threads/mm adjacent the first end 26 to between approximately 0.1 to 1 threads/mm at the second end 28. The shaft 16 has an average diameter of between 50 mm and 0.7 mm, more preferably between 20 mm and 3 mm, and in some arrangements between approximately 4.9 mm and 5.1 mm. Either or both of the forward external thread 50 and the rear external thread has a major diameter of between 52 mm and 0.9 mm, more preferably between 22 mm and 5 mm, and in one arrangement between approximately 5.0 mm and 5.2 mm. However, the specific dimensions provided herein are only exemplary of one optional exemplary arrangement, and the invention is not limited to the specific dimensions provided.

Figure 4:
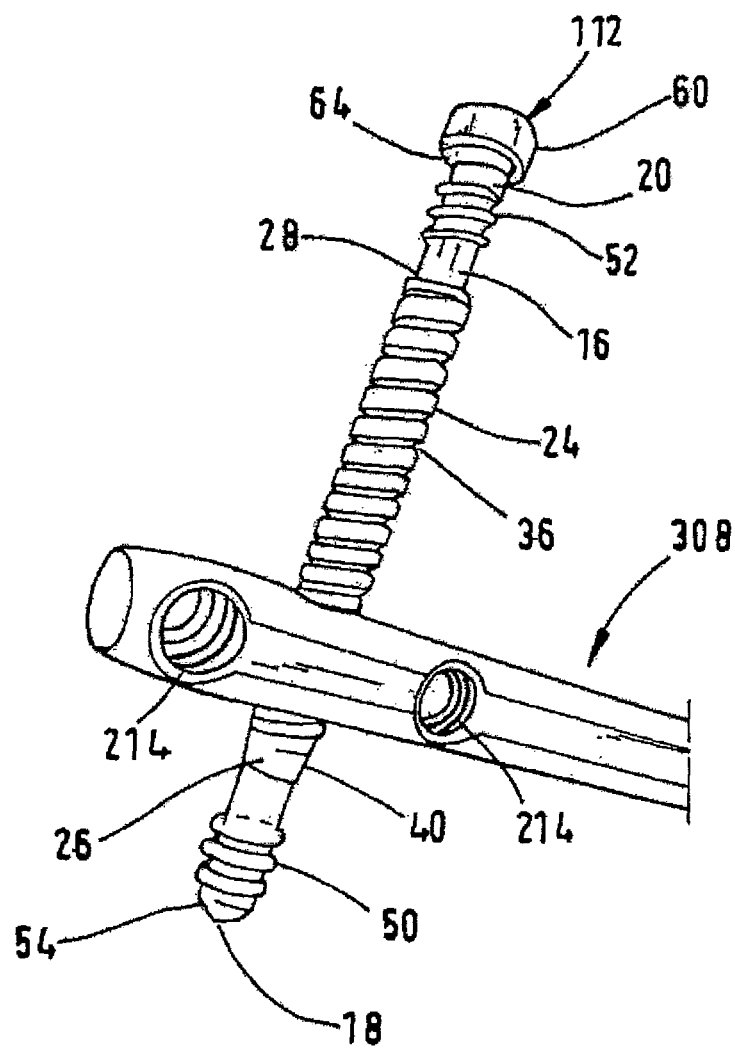
FIGS. 4 and 5 are orthogonal partial views of another orthopedic fastening system with an orthopedic locking screw operably disposed through a bore of an intramedullary nail.
Figure 5:
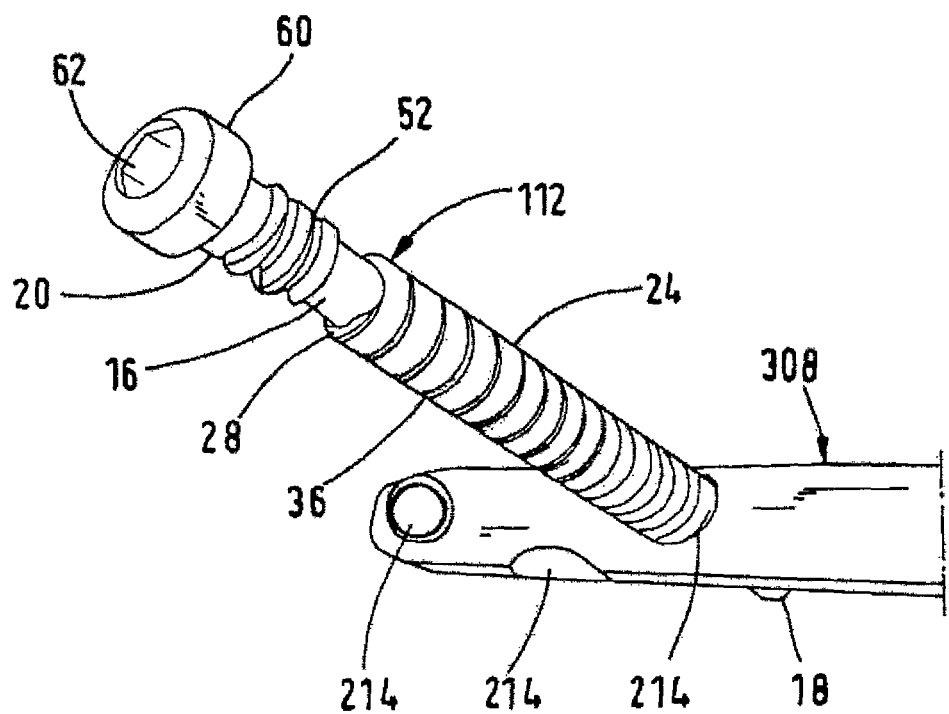

FIGS. 4 and 5 show different views of another orthopedic fastening system in which the orthopedic locking screw 112 is operably engaged with, such as in and/or through, a bore 214 of an orthopedic implant in the form of an intramedullary nail 308. The intramedullary nail 308 includes at least one, and in this example, three or optionally more bores 214. The bores 214 which may be threaded bores and/or include any and/or all of the features of the bores 14 and 114 previously described herein. The orthopedic locking screw 112 is the same as described previously. In some arrangements, this orthopedic fastening system may also or alternatively include the orthopedic locking screw 10 operably engaged through any one of the bores 214. As with the previously described systems, the casing 24 develops a press-fit against the interior of the bore 214 so as to reduce or eliminate movement between the shaft 16 and the body of the intramedullary nail 308, in any of the manners described previously herein. Remaining aspects of this system are substantially similar as corresponding portions previously described herein and is not repeated here for the sake of brevity.

Next, a method of securing an orthopedic locking screw to a bore is described according to one aspect of the disclosure. The method is described with reference to the arrangement of FIG. 3. However, this method is not limited to the orthopedic locking screw 112 and the orthopedic implant 208. Rather, this method may be used to engage any one of the orthopedic screws, such as 12 and 112, to any one of the threaded bores, such as 14, 114, or 214 disposed in any one of the orthopedic implants, such as 34, 208, and/or the intramedullary nail 308, disclosed herein. Thus, the following description, while focused mainly on the combination shown in FIG. 3 for exemplary reasons, also refers to other arrangements. It is understood, however, that this method is not limited to the exact description of these particular arrangements, but can be applied to any arrangement in a manner that would be understood by the ordinarily skilled person.

In a first step, the first end 18 of the shaft 16 is inserted into the bore 114 of the orthopedic implant 208.

The shaft 16 is advanced into the bore 114 in any sufficient manner. If the forward external threads 50 operably engage the internal thread 38, the shaft 16 may be rotated, for example with a rotational drive tool engaged with the drive member 20, to advance the first end 18 of the shaft into and/or through the bore 114. If the forward external thread 50 does not operably engage the internal thread 38, or if the orthopedic locking screw 112 does not have a forward external thread 50, the shaft 16 may be advanced in other ways, for example by driving or drilling.

The shaft 16 is advanced through the bore 114 in any of these manners, as appropriate, so as to engage the casing 24 with the bore 114.

Next, the drive member 20 is rotated, which rotates the shaft 16 and the casing 24, so as to operably engage the casing 24 with the bore 114. The bore 114 (or the bore 14) deforms the casing 24 radially and/or axially, thereby developing a deformable press-fit of the casing against the bore 114 in a radial pressure direction and/or an axial pressure direction. Where the casing 24 includes the deformable thread 36, the deformable thread 36 may further advance the shaft 16 through the bore 114 by operable engagement of the deformable thread 36 with the internal thread 38 and/or the circumferential rib 70. Where the casing 24 has a smooth outer surface, the internal thread 38 may still operate to advance the shaft 16 through the bore 114 by engagement with and deformation of the outer surface of the casing 24.

As the casing 24 advances through the bore 114, a press-fit pressure between the casing 24 and the interior surface of the bore develops. The press-fit pressure may increase as the casing 24 advances through the bore 114. For example, where the deformable thread 36 has a variable pitch, increased axial press-fit pressure may be developed as the casing 24 advances through the bore 114. Where the deformable thread has an increasing outside diameter, such as an increasing minor diameter and/or major diameter, increased radial press-fit pressure may be developed as the casing 24 advances through the bore 114. Alternatively, the outer surface of the casing 24 may be cylindrical and any deformable thread 36 have a constant pitch along the length of the casing, in which case the press-fit pressure may remain substantially constant as the casing 24 advances through the bore 114 (or 14). The forward external thread 50 operates to advance, (e.g., by pulling) the shaft 16 and the casing 24 through the bore 114 by engaging with bone on the opposite side of the orthopedic implant 208. Additionally, the rear external thread 52 may also operate to advance (e.g., by pushing) the shaft and the casing 24 through the bore 114 by engaging with the bone on the insertion side of the orthopedic implant 208.

When the orthopedic locking screw 112 is disposed in a selected position, the press-fit pressure between the casing 24 and the internal surface of the bore 114 prevents or reduces undesired rotational movement and/or lateral movement and/or axial movement of the orthopedic locking screw 112 relative to the bore 114, and optionally also to the orthopedic implant 208.

The orthopedic locking screws of the present disclosure provide in some circumstances a tighter fit with the bore of, for example, an orthopedic implant, such as an intramedullary nail or a plate, or a bone, than has been heretofore achievable with a single orthopedic screw. As a result, undesired movement and shifting between the connected bone portions and/or the orthopedic implant may be reduced, thereby improving the healing process of the bone. In addition, the improved locking capability of the orthopedic locking screws may allow the number of locking elements needed in an orthopedic fastening system to be decreased. Other technical advantages and/or usefulness are also possible.

The features described in relation to the exemplary arrangements shown in the drawing can be readily combined to result in different embodiments, as suggested previously above. It is apparent, therefore, that the present disclosure may be varied in many ways. Such variations are not to be regarded as a departure from the scope of the invention, and all modifications within the scope of the appended claims are intended to be expressly included therein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic fastening system, comprising:
an orthopedic implant comprising a bore; and
an orthopedic locking screw configured to be retained inside the bore, the orthopedic locking screw comprising:
a shaft extending along an axis between a first and a second end, the first end sized to be received in the bore;
a drive member disposed at the second end;
a casing secured to and rotationally fixed around an outer surface of the shaft in a non-secured state of the screw, wherein the casing is formed of a plastically deformable material, the casing having a first end proximate the first end of the shaft and a second end proximate the second end of the shaft; and
a forward external thread disposed on the shaft between the first end of the casing and the first end of the shaft, wherein the casing has an outer cross-sectional width (W1) that is larger than a smallest inside cross-sectional width of the bore and forms a press-fit pressure against the bore when operably disposed in the bore, and
wherein the casing comprises a deformable thread disposed along an outer surface of the casing, wherein the deformable thread is an external thread that is configured to engage an internal thread feature of the bore.

2. The orthopedic fastening system of claim 1, wherein the outer cross-sectional width of the casing is larger than a largest outside diameter of the first end of the shaft and any threads disposed on the first end of the shaft.

3. The orthopedic fastening system of claim 1, wherein the shaft comprises a polygonal or other non-circular profile that prevents the casing from rotationally slipping on the shaft.

4. The orthopedic fastening system of claim 1, wherein the deformable thread has a minor diameter (Dmin) that is constant along the length of the deformable thread.

5. The orthopedic fastening system of claim 1, wherein the deformable thread is a continuous thread extending from adjacent the first end of the casing to the second end of the casing.

6. The orthopedic fastening system of claim 1, wherein the first end of the casing is tapered radially inwardly toward the outer surface of the shaft.

7. The orthopedic fastening system of claim 1, wherein the shaft includes a groove, wherein the groove extends circumferentially around the shaft, and wherein the casing is disposed in the groove.

8. The orthopedic fastening system of claim 7, wherein the groove extends axially along the shaft between a first shoulder proximate the first end of the shaft and a second shoulder proximate the second end of the shaft, wherein the first and second shoulders secure or assist securing the casing on the shaft.

9. The orthopedic fastening system of claim 8, wherein the first end of the casing engages the first shoulder and the second end of the casing engages the second shoulder.

10. The orthopedic fastening system of claim 7, wherein a radially inner surface of the casing is secured against a radially outer surface of the groove.

11. The orthopedic fastening system of claim 1, wherein the orthopedic locking screw includes a rear external thread disposed on the shaft between the second end of the shaft and the second end of the casing.

12. The orthopedic fastening system of claim 11, wherein the outer diameter of the casing is larger than the outer diameter of at least one of the forward and rear external threads.

13. The orthopedic fastening system of claim 11, wherein at least one of the forward external thread and the rear external thread is axially spaced apart from the casing.

14. The orthopedic fastening system of claim 1, wherein the orthopedic locking screw includes a tip disposed at the first end of the shaft, wherein the tip comprises a self-tapping feature.

15. The orthopedic fastening system of claim 1, wherein the drive member comprises:
a head configured to engage with a rotational drive member, the head forming a shoulder extending radially outwardly from an outer surface of the shaft to an outer surface of the head.

16. The orthopedic fastening system of claim 1, wherein each of the shaft and the casing is formed of a biocompatible material, wherein the material of the casing is softer than the material of the shaft, the material of the casing comprising at least one of a plastic and a metal, and the material of the shaft comprising at least one of a plastic, a metal, and a ceramic.

17. The orthopedic fastening system of claim 1, wherein the orthopedic implant is formed of a biocompatible material.

18. The orthopedic fastening system of claim 1, wherein the deformable thread has an outside diameter that is larger than a corresponding inside diameter of the bore.

19. The orthopedic fastening system of claim 1, wherein the deformable thread has a variable pitch that varies along the direction of the axis.

20. The orthopedic fastening system of claim 1, wherein the orthopedic implant comprises an intramedullary nail.

21. A method of securing an orthopedic screw in a bore of an orthopedic implant, the method comprising the steps:
providing an orthopedic locking screw comprising a shaft extending along an axis between a first end and a second end, the first end sized to be received in the bore; a drive member disposed at the second end; a casing secured to and rotationally fixed around an outer surface of the shaft in a non-secured state of the screw, wherein the casing is formed of a plastically deformable material, the casing having a first end proximate the first end of the shaft and a second end proximate the second end of the shaft; and a forward external thread disposed on the shaft between the first end of the casing and the first end of the shaft, wherein the casing has an outer cross-sectional width (W1) that is larger than a smallest inside cross-sectional width of the bore;
inserting the first end of the shaft into the bore;
engaging the casing with the bore;
rotating the drive member to rotate the shaft and the casing so as to operably engage the casing with the bore, thereby achieving a deformable press-fit of the casing against the bore, wherein the casing comprises a deformable thread disposed along an outer surface of the casing, wherein the deformable thread is an external thread that operably engages the bore so as to form a mechanical interfit with the bore.

22. The method of claim 21, wherein a minor diameter (Dmin) of the deformable thread is larger than a smallest inner diameter of the bore, and wherein rotating the drive member causes the deformable press-fit to include a radially directed pressure between the casing and the smallest inner diameter.

23. The method of claim 21, wherein the deformable thread has a variable pitch that varies along the direction of the axis, and wherein rotating the drive member causes the deformable press-fit to include an axially directed pressure between the casing and the deformable thread.

* * * * *